United States Patent [19]
Elliott

[11] Patent Number: 5,286,718
[45] Date of Patent: Feb. 15, 1994

[54] METHOD AND COMPOSITION FOR AMELIORATING TISSUE DAMAGE DUE TO ISCHEMIA AND REPERFUSION

[75] Inventor: Gary T. Elliott, Hamilton, Mont.
[73] Assignee: RIBI Immunochem Research, Inc., Hamilton, Mont.
[21] Appl. No.: 815,250
[22] Filed: Dec. 31, 1991
[51] Int. Cl.$^5$ ........................................... A61K 31/715
[52] U.S. Cl. ..................................... 514/54; 514/921
[58] Field of Search ................................ 514/54, 921
[56] References Cited

U.S. PATENT DOCUMENTS

| | | | |
|---|---|---|---|
| 4,436,727 | 3/1984 | Ribi | 424/177 |
| 4,912,094 | 3/1990 | Myers et al. | 514/54 |
| 4,976,959 | 12/1990 | Berger, Jr. et al. | 424/94.2 |
| 4,985,241 | 1/1991 | Zimmerman et al. | 424/85.1 |

OTHER PUBLICATIONS

Ambrosio, et al. *Circulation*, vol. 76, No. 4, pp. 906–915 (Oct. 1987).
Ding, *The Journal of Immunology*, vol. 141, No. 7, pp. 2407–2412, Oct. 1, 1988.
Beckman et al., *Proct. Natl. Acad. Sci. USA*, vol. 87, pp. 1620–1624, Feb. 1990.
Asayama, et al. *Am. J. Physiol.*, 249 (Cell Physiol. 18): C393-C397 (1985).
Berg, et al. *J. Appl. Psysiol.*, 68(2):549–553 (1990).
Allison, et al. *J. Appl. Physiol.* 69(2) 1990.
Berg, et al. *Proc. Soc. Exp. Biol. & Medicine*, 193:167–170 (1990).
Welbourn, et al. *The Journal of Immunology*, vol. 145, 1906–1911, No. 6 (Sep. 15, 1990).
Mullane, et al. *The Journal of Pharmacology and Experimental Therapeutics*, Col. 228, No. 2 (1984).
Nelson, et al. *Surgery*, 110:2 (Aug. 1991).
Wendel, et al. *Biochemical Pharmacology*, vol. 36, No. 16, pp. 2637–2639 (1987).
Entman, et al., *The FASEB Journal*, vol. 5, pp. 2529–2537 (Aug. 1991).
Braunwald et al., *J. Clin. Invest.*, vol. 76, Nov. 1985, 1713–1719.
Bensard, et al., *Journal of Surgical Research*, vol. 48, No. 6, Jun. 1990.
Brown, et al., *Proc. Natl. Acad. Sci. USA*, vol. 86, pp. 2516–2520, Apr. 1989.
Brown, et al., *Proc. Natl. Acad. Sci. USA*, vol. 87, pp. 5026–5030, Jul. 1990.
Woodward et al., *J. Mol. Cell Cardiol.* 17, 485–493 (1985).
Weishaar, et al., *Journal of Molecular and Cellular Cardiology*, 12, 993–1009 (1980).
Jolly, et al. *Journal of Cardiovascular Pharmacology*, 4:441–448 (1982).
Jolly, et al., *Circulation Research*, vol. 54, No. 3, pp. 277–285 (Mar. 1984).
Heiman, et al., *J. Lab Clin. Med.*, pp. 237–241 (Aug. 1990).
Bensard, et al. "Endotoxin Induces Left Ventricular Depression In the Isolated Perfused Rat Heart" Submitted AJP Apr. 27, 1990.
Abstract: Heiman et al., *Clinical Research*, vol. 36, No. 6, p. 847A (1988).
Abstract: Hirose, et al., *Macrophage Biology III*, A1854:939 1988.
Abstract: Nicolini, et al., *JACC*, vol. 25, No. 2, Feb. 1990:32A 1987.
Abstract: Hale et al., *JACC*, vol. 26, No. 2, Feb. 1990:32A 1987.
Abstract: Simpson, *J. Lab. Clin. Med.*, 110(1) pp. 13–30 (Jul. 1987).
Abstract: Simpson, *Fed. Proc.* 46(7) pp. 2413–2421 (May 15, 1987).
Elliott et al., "The D-Galactosamine Loaded Mouse and Its Enhanced Sensitivity to LPS and Monosphosphoryl Lipid A: A Role for Superoxide" (Running Title: Factors of Galactosamine Sensitization to MPL) 1990.

*Primary Examiner*—Frederick E. Waddell
*Assistant Examiner*—Gregory Hook
*Attorney, Agent, or Firm*—Zarley, McKee, Thomte, Voorhees, & Sease

[57] ABSTRACT

A method of inhibiting tissue damage in warm blooded animals related to reperfusion of tissues after extended periods of ischemia is presented. The method comprises treatment prior to a planned ischemic event or up to six hours after an unplanned ischemic event with an effective amount of monophosphoryl lipid A or 3-deacylated monophosphoryl lipid A. Pharmaceutical compositions for the treatment are also disclosed.

12 Claims, 1 Drawing Sheet

METHOD AND COMPOSITION FOR AMELIORATING TISSUE DAMAGE DUE TO ISCHEMIA AND REPERFUSION

BACKGROUND OF THE INVENTION

Cellular damage to aerobic organ tissues is well recognized as a consequence of prolonged ischemia, whether endogenous as in the case of a spontaneous coronary artery occlusion, or iatrogenic such as with open heart, coronary bypass surgery, or similar transplant procedures with other organs such as the lung, liver, kidney, and gastrointestinal tract. The degree and duration of the ischemia causing event are relevant to the amount of cell death and/or reversible cellular dysfunction. It is also known that much of the tissue damage, in fact, occurs upon reperfusion (i.e., resumption of blood flow) and re-oxygenation of the previously anoxic tissue. The phenomenon, referred to as reperfusion injury, has been the subject of considerable recent study prompted by medical advances particularly in the treatment of myocardial events such as myocardial infarction (MI) and other remedial procedures such as coronary bypass, other open heart surgeries, and organ transplants.

As a side product of normal aerobic respiration, electrons are routinely lost from the mitochondrial electron transport chain. Such electrons can react with molecular oxygen to generate the reactive free radical superoxide which through other reaction steps in the presence of hydrogen peroxide and iron produces the extraordinarily reactive and toxic hydroxyl radical. Metabolically active aerobic tissues possess defense mechanisms dedicated to degrading toxic free radicals before these reactive oxygen species can interact with cellular organelles, enzymes, or DNA, the consequences of which could, without such protective mechanisms, be cell death. These defense mechanisms include the enzymes superoxide dismutase (SOD) which disproportionates superoxide, catalase which degrades hydrogen peroxide, and the peptide glutathione which is a non-specific free radical scavenger.

While not fully understood, it is believed that with prolonged ischemia of metabolic tissues (twenty minutes or more) and subsequent reperfusion, a complex group of events occurs. Initially during the ischemic period, intracellular anti-oxidant enzyme activity appears to decrease, including that of SOD, catalase, and glutathione. There is also an indication that the level of xanthine oxidase activity concomitantly increases in vascular endothelial tissue during the ischemic event. The combination of enhanced ability to produce oxygen free radicals (via enhanced xanthine oxidase activity) and reduced ability to scavenge the same oxygen radicals (via reduced SOD, catalase and glutathione activity) greatly sensitizes the ischemic cell to an oxidative burst, and hence damage, should these cells be subsequently reperfused with blood and therefore oxygen. This oxidative burst occurring within seconds to minutes of reperfusion could result in reversible and irreversible damage to endothelial cells and other cells constituting the ischemic-reperfused organ matrix. If, for example, the heart is the organ under consideration, reversible oxidative damage can contribute to myocardial stunning, whereas irreversible damage presents itself as a myocardial infarction. Attendant with this initial oxidative burst is oxidation damage to cell membranes. Lipid oxidation in cell membranes appears to play a role in neutrophil chemotaxis to post-ischemic areas. Such activated neutrophils adhere to vascular endothelium, induce the conversion of xanthine dehydrogenase to xanthine oxidase within said endothelial cells, and further aggravate loss of endothelial integrity. Activated neutrophils also migrate out of the vasculature into myocardial interstitial spaces where the inflammatory cells can directly kill myocytes. Additionally, perturbations in normal calcium mobilization from sarcoplasmic reticulum as a consequence of ischemia-reperfusion contribute to reversible myocardial dysfunction referred to as myocardial stunning.

"Stunning" in lay terms refers to decreased, yet reversible, pump efficiency in the case of the heart which leads to decreased cardiac output and, hence, the symptomatology of suboptimal organ perfusion. Reperfusion of ischemic myocardial tissue may also cause electrophysiologic changes, including potentially lethal arrhythmias.

Therefore, the consequences of ischemia-reperfusion events are reversible and irreversible cell damage, cell death, and decreased organ functional efficiency. More specifically, in the case of myocardial reperfusion injury, the consequences include myocardial stunning, arrhythmias, and infarction, and as a sequela, cariogenic shock and potentially congestive heart failure.

The paradox of cellular damage associated with a limited period of ischemic anoxia followed by reperfusion is that cell damage and death appear not only likely to directly result from the period of oxygen deprivation but, additionally, as a consequence of re-oxygenation of tissues rendered highly sensitive to oxidative damage during the ischemic period. Reperfusion damage begins with the initial oxidative burst immediately upon reflow and continues to worsen over a number of hours as inflammatory processes develop in the same post-ischemic tissues. Efforts dedicated to decreasing sensitivity of post-anoxic cells to oxidative damage and, additionally, efforts to reduce inflammatory responses in these same tissues have been shown to reduce the reversible and irreversible damage to post-anoxic reperfused organs. A combination of methods to reduce both the initial oxidative burst and subsequent inflammation associated damage could provide synergistic protection against reperfusion injury.

With respect to the treatment of MI patients, a common therapy now used is to employ thrombolytics such as streptokinase and t-PA. U.S. Pat. No. 4,976,959 discloses the administration of t-PA and SOD to inhibit tissue damage during reperfusion and/or percutaneous transluminal coronary angioplasty during heart attacks to restore regional blood flow. Thus, an increasing number of patients are being exposed to the likelihood of reperfusion injury and its effects, particularly cardiac patients.

While exogenously administered, SOD is known to destroy free hydroxyl radicals and, therefore, in theory helps alleviate the oxidative burst which occurs upon reperfusion, in fact it does not have broad clinical applicability, has limited effectiveness, and to date has been restricted in its application to amelioration of ischemia-reperfusion injury involving the heart.

There is, therefore, a continuing need for the development of ischemia reperfusion-injury attenuating treatments which have broader applicability and greater effectiveness. For example, there are many ischemic reperfusion (re-oxygenation) events besides MI where an effective reperfusion injury protective agent could be utilized. Such events include organ transplants, traumatic limb amputation and reattachment, CNS trauma, Reye's syndrome, gut infarct, and other cardiac surgical procedures such as bypass surgery, value replacement, septal defect repairs.

Reperfusion injury to organs other than the heart will generally manifest itself in substantially reduced efficiency of function, a consequence of which may be premature degeneration of the organ. Additionally, transplanted organs experience enhanced rejection rates if there is significant underlying reperfusion injury.

As discussed briefly above, while the precise mechanism of reperfusion injury has not been clearly defined, mounting data, most of which has been gathered in various cardiac model studies, indicate that the generation of oxygen-derived free radicals, including superoxide anion $(O_2)_1$, the hydroxyl free radical (—OH) and $H_2O_2$, results as a consequence of the reintroduction of molecular oxygen with reperfusion and plays an important role in tissue necrosis. Agents which either decrease the production of these oxygen derived free radicals (including allopurinol and deferroxamine) or increase the catabolism of these materials such as superoxide dismutase, catalase, glutathione, and copper complexes, appear to limit infarct size and also may enhance recovery of left ventricular function from cardiac stunning.

Brown et al. conducted experiments whereby it was shown that hearts isolated from rats pretreated with endotoxin twenty-four hours prior to ischemia and reperfusion showed increased myocardial catalase activity with consequent increased myocardial function as assessed by measurement of ventricular developed pressure contractility (+dp/dt) and relaxation rate (−dp/dt) compared to control hearts, as evidence of decreased injury. (See *Proc. Natl. Acad. Sci. USA*, Vol. 86, pp 2516-2520, April 1989, Physiological Sciences). (See also Bensard, et al., Endogenous Tissue Antioxidant Enzyme Activity, *Journal of Surgical Research*, Vol. 48, No. 6, June 1990.)

Berg et al. noted that rats pretreated with endotoxin were protected against lung injury during hyperoxia by pretreatment with endotoxin. They observed increased levels of tumor necrosis factor (TNF) and interleukin-1 (IL-1) in sera. (See *J. Appl. Physiyol.* 68(2): 549-553, 1990.)

Notwithstanding observations of the protective effect of endotoxin as discussed above, Smith conducted experiments to compare the protective effects of endotoxin, diphosphoryl lipid and monophosphoryl lipid A against lethal intrathoracic edema produced by continuous exposure to hyperoxia conditions. Sprague-Dawley rats were pretreated with one of the materials 72 hours prior to hyperoxia exposure. It was observed that toxic endotoxin and toxic diphosphoryl lipid A protected the rats against oxygen toxicity, but that non-toxic monophosphoryl lipid A actually potentiated pulmonary oxygen toxicity. (See *Research Communications in Chemical Pathology and Pharmacology*, Vol. 62, No. 2, Nov. 1988).

A variety of agents have been identified through preclinical investigations which appear to have the potential to provide some benefit in respect to reperfusion injury. Unfortunately, when applied to the human clinical setting, the results have been disappointing. SOD performed poorly at reducing myocardial infarct size in the clinical setting. A short half-life, poor tissue distribution, and consequently primarily a protective effect on vascular endothelium restricted clinical utility. Efforts to improve the half-life of SOD by forming the polyethylene glycol conjugate did not improve protective activity. Allopurinol has demonstrated some efficacy in early human studies involving renal transplants. Other agents entering human clinical trials include a monoclonal antibody to the neutrophil adhesion molecule CD18, a complement receptor antagonist, fluorinated hydrocarbons, and adenosine or adenosine agonists. However, these and other therapies under consideration have yet to exhibit the desired clinically useful attributes.

The pathogenesis of reperfusion injury is very complex, including depletion of anti-oxidant enzymes, alterations in xanthine oxidase activity, alterations in calcium mobilization, activation, chemotaxis and localization of inflammatory cells (neutrophils), and alterations in vascular permeability. Thus, prior to the present invention effective amelioration of reperfusion injury may require the use of multiple therapeutic agents each one of which acts to modify only one or at best a few or the aspects of pathogenesis. SOD or catalase administration supplements the depletion of these single enzymes. Allopurinol is a xanthine oxidase inhibitor. Adenosine restores ATP levels in post-ischemic tissue. Monoclonal antibodies to CD18 and complement receptor antagonist block neutrophil adhesion to vascular endothelium. The present invention which interferes with multiple aspects of reperfusion injury represents a substantial advance in the art.

It can therefore be seen that there is a need for a safe, effective composition having broad applicability to prevent or ameliorate the harmful effects of reperfusion with minimal side effects. It is a primary object of the present invention to fulfill this need.

Another object of the present invention is to provide a method for providing a high degree of protection for warm blooded animals against the harmful effects of reperfusion after a prolonged period of ischemia without the side effects attendant with therapies presently available.

Still another objective of the present invention is to provide a pharmaceutically acceptable carrier composition which can be used for intravenous administration of the compositions of the present invention without any significant undesirable side effects and without adversely affecting antigenic or immune stimulating properties.

These and other objects and benefits of the present invention will be apparent to those skilled in the art from the further description and accompanying claims.

SUMMARY OF THE INVENTION

Figure 1:
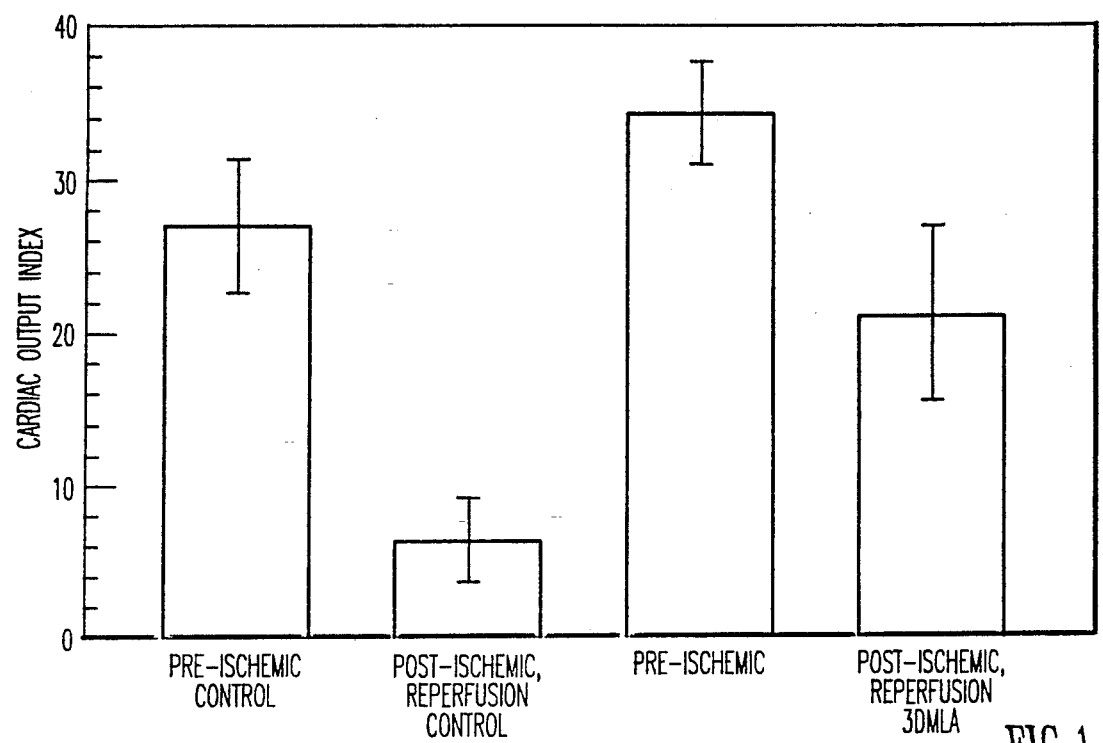
FIG. 1 shows rat heart maximal recovery of baseline function after ischemia and reperfusion with monophosphoryl lipid A (MLA) administered twenty-four or seventy-two hours prior to ischemia.

The present invention provides for pharmaceutical compositions and method of use thereof for the prevention or amelioration of the harmful effects of blood reperfusion following a prolonged period of organ ischemia. The compositions and method involve administering an effective amount of a refined detoxified endotoxin selected from the group consisting of monophosphoryl lipid A (MLA) and 3 deacylated monophosphoryl lipid A (3DMLA) in a suitable vehicle to a warm blooded mammal at a time sufficient to enable said composition to disperse to the area at risk of reperfusion injury and to elicit its protective activities.

DETAILED DESCRIPTION OF THE INVENTION

In accordance with the present invention the active compound for treating warm blooded mammals to minimize reperfusion injury is a refined detoxified endotoxin selected from the group consisting of monophosphoryl lipid A (MLA) and 3 deacylated monophosphoryl lipid A (3DMLA). Both MLA and 3DMLA are known and need not be described in detail herein. See for example U.S. Pat. No. 4,436,727 issued Mar. 13, 1984, assigned to Ribi ImmunoChem Research, Inc, which discloses monophosphoryl lipid A and its manufacture. U.S. Pat. No. 4,912,094 to Myers et al., also assigned to Ribi ImmunoChem Research, Inc., embodies 3 deacylated monophosphoryl lipid A and a method for its manufacture. Disclosures of each of these patents with respect to MLA and 3DMLA are incorporated herein by reference.

Without going into the details of the prior incorporated by reference patents, monophosphoryl lipid A (MLA) as used herein is derived from lipid A, a component of enterobacterial lipopolysaccharides (LPS), a potent but highly toxic immune system stimulator.

Edgar Ribi and his associates achieved the production of monophosphoryl lipid A (MLA) referred to originally as refined detoxified endotoxin (RDE). MLA is produced by refluxing an endotoxin extract (LPS or lipid A) obtained from heptoseless mutants of gram-negative bacteria in mineral acid solutions of moderate strength (0.1 N HCl) for a period of approximately 30 minutes. This treatment results in the loss of the phosphate moiety at position 1 of the reducing end glucosamine.

Coincidentally, the core carbohydrate is removed from the 6 position of the non-reducing glucosamine during this treatment. The resulting product (MLA) exhibits considerable attenuated levels of the endotoxic activities normally associated with the endotoxin starting material, such as pyrogenicity, local Shwarzman reactivity, and toxicity as evaluated in the chick embryo 50% lethal dose assay ($CELD_{50}$). However, it unexpectedly retains the functionality of lipid A and LPS as an immunostimulant. Monophosphoryl lipid A is available from Ribi ImmunoChem Research, Inc., Hamilton, Montana 59840.

Another detoxified endotoxin which may be utilized in the practice of the present invention is referred to as 3-deacylated monophosphoryl lipid A (3DMLA). 3DMLA is known as set forth in U.S. Pat. No. 4,912,094, and differs from MLA in that there is selectively removed from the MLA molecule the B-hydroxymyristic acyl residue that is ester linked to the reducing-end glucosamine at position 4 under conditions that do not adversely affect other groups.

The 3DMLA molecule is a composite or mixture of a number of fatty acid substitution patterns, i.e., heptaacyl, hexaacyl, pentaacyl, etc., with varying fatty acid claim lengths. A representative structure of this material is shown in the referenced −094 patent. Thus, various forms of 3-deacylated material, including mixtures thereof, are encompassed by this invention. The lipid A backbone that is illustrated in the −094 patent corresponds to the product that is obtained by de-3-O-acylation of heptaacyl lipid A from S. minnesota R595. Other fatty acid substitution patterns are encompassed by this disclosure; the essential feature is that the material be de-3-O-acylated.

The modified 3-DMLA utilized in the present invention is prepared by subjecting the compounds to alkaline hydrolysis under conditions that result in the loss of but a single fatty acid from position 3 of the lipid A backbone. The B-hydroxymyristic at position 3 is unusually labile in alkaline media. It requires only very mild alkaline treatment to completely de-3-O-acylate lipid A. The other ester linkages in lipid A require somewhat stronger conditions before hydrolysis will occur so that it is possible to selectively deacylate these materials at position 3 without significantly affecting the rest of the molecule. The reason for the unusual sensitivity to alkaline media of the ester-linked B-hdyroxymyristic at position 3 is not known at this time.

Although alkaline hydrolysis procedures are known, it is important to choose conditions that do not cause further hydrolysis beyond the ester linkage to the B-hydroxymyristic at position 3.

In general the hydrolysis can be carried out in aqueous or organic media. In the latter case, solvents include methanol (alcohols), dimethyl sulfoxide (DMSO), dimethylformanide (DMF), chloroform, dichloromethane, and the like, as well as mixtures thereof. Combinations of water and one or more of the mentioned organic solvents also can be employed.

The alkaline base can be chosen from among various hydroxides, carbonates, phosphates and amines. Illustrative bases include the inorganic bases such as sodium hydroxide, potassium hydroxide, sodium carbonate, potassium carbonate, sodium bicarbonate, potassium bicarbonate, and the like, and organic bases such as alkyl amines, and include but are not limited to diethylamine, triethylamine, and the like.

In aqueous media the pH is typically between approximately 10 and 14 with a pH of about 12 to about 13.5 being the preferred range. The hydrolysis reaction is typically carried out at a temperature of from about 20° C. to about 80° C., preferably about 50° C. to 60° C. for a period of about 10 to about 30 minutes. For example, the hydrolysis can be conducted in 3% triethylamine in water at room temperature (22°–25° C.) for a period of 48 hours. The only requirement in the choice of temperature and time of hydrolysis is that de-O-acylation occurs to remove only the B-hydroxymyristic at position 3.

In practice it has been found that a particularly desirable hydrolysis method involves dissolving lipid A or monophosphoryl lipid A in chloroform:methanol 2:1 (v/v), saturating this solution with an aqueous buffer consisting of 0.5M $Na_2CO_3$ at pH 10.5, and then to flash evaporate the solvent at 45° C.–50° C. under a vacuum for an aspirator (approximately 100 mm Hg). The resulting material is selectively deacylated at position 3. This process can also be carried out with any of the inorganic bases listed above. The addition of a phase transfer catalyst, such as tetrabutyl ammonium bromide, to the organic solution prior to saturating with the aqueous buffer may be desirable in some cases.

It has been observed that MLA and 3DMLA when administered to animals or humans at "safe doses", induce the elaboration into the serum of tumor necrosis factor (TNF). TNF has been identified in the literature as an excellent inducer of intracellular, manganous superoxide dismutase (MnSOD). This enzyme is of great importance to a cell's ability to avoid the cytotoxic effects of superoxide produced in mitochondria as a consequence of aerobic respiration. It is therefore realistic to predict that administration of MLA or 3DMLA to animals or humans could result in the indirect induction of intracellular MnSOD in response to TNF elaboration from activated macrophages.

Monophosphoryl lipid A also has been reported to desensitize neutrophils, thereby blocking their ability to mount an oxidative burst in response to a subsequent endotoxin exposure, and one might hypothesize, in response to other neutrophil activators. Monophosphoryl lipid A and 3DMLA also protect D-galactosamine loaded mice from a potentially lethal endotoxin challenge. The inventor has previously reported in the literature that lethality associated with endotoxin challenge in the D-galactosamine loaded mouse is due in part to superoxide production in the animal. A natural question arising from these observations is: could pretreatment with MLA or 3DMLA, known to protect the D-galactosamine loaded mouse from the lethality of a subsequent endotoxin challenge, be reducing the oxidative burst damage associated with endotoxin challenge in this mouse model.

The above-mentioned observations do not exemplify that MLA or 3DMLA ameliorate reperfusion injury, but when experimentation on relevant animal models of reperfusion injury did illustrate MLA and 3DMLA display protective activity, the above observations shed some light on potential mechanisms of action. These observations additionally suggest that MLA and 3DMLA may possess multiple mechanisms for reperfusion injury protection, providing synergistic efficacy and hence a clear advantage for the described indication over the prior art.

The method of the present invention embodies the administration to warm blooded mammals, preferably humans, of a pharmacologically effective amount of a composition comprising a detoxified endotoxin selected from the group consisting of MLA and 3DMLA with a pharmaceutically effective carrier. As used herein, the term pharmaceutically effective amount means the amount of the composition that is sufficient to elicit a demonstrable patient response, i.e., partial or complete protection against reperfusion injury.

The administration may be by any suitable route with parenteral intravenous or intramuscular administration being preferred. The precise dosage will depend upon the particular detoxified endotoxin utilized and the route of administration. When administered parenterally to a human patient, the preferred dose of the compositions of the present invention is within the range of from about 1.0 ug/kg of body weight to 100 ug/kg of body weight, with from about 1.0 ug/kg of body weight to about 35 ug/kg of body weight being preferred and with dosages of under 20 ug/kg of body being most preferred.

The method of the present invention contemplates single or multiple doses, depending upon the particular situation. The preferred route of administration and dosage regimes for a given case may be ascertained by relatively routine experimentation involving clinical trials.

The term "pharmaceutically acceptable carrier" as used in this description means a medium which does not interfere with the medicinal activity of the active ingredient and is not toxic to the patient to whom it is administered. Examples of a preferred carrier for intravenous use include 10% USP ethanol, 40% USP propylene glycol and the balance USP water for injection. Another acceptable carrier includes 10% USP ethanol and USP water for injection; yet another acceptable carrier is 0.01-0.1% triethanolamine in USP water for injection. Still other acceptable carriers are pharmaceutically acceptable liposomes in USP water for injection or intravenous vegetable oil in water emulsions. One point worthy of mention with regard to the carrier is that it has been found, so far, that normal saline solution cannot be used with the active components of the present invention since MLA precipitates out in normal saline solution. These injectable solutions can be given by slow intravenous push or further diluted in 5% dextrose in water for injection and infused intravenously. Pharmaceutically acceptable parenteral solvents are such as to provide a solution or dispersion of the active ingredients of the present invention such that the solution or dispersion may be filtered through a 5 micron filter without removing the active ingredient.

Carriers for intramuscular use would replace USP water for injection in the above formulations with an acceptable isotonic solution such as 5% dextrose in water for injection. MLA or 3DMLA entrapped in liposomes could alternatively be further solubilized for intravenous or intramuscular use in normal saline, as precipitation of the active ingredient will not occur in saline when the solability of MLA or 3DMLA is stabilized in liposomes.

The oxidative damage of reperfusion injury can manifest itself as a continuum proceeding from reversible organ dysfunction to cell death. Certain clinical scenarios of reperfusion injury can lead to predominantly reversible damage. Organ transplantation, open heart, or coronary bypass surgical procedures are examples of clinical situations where global organ ischemia followed by reperfusion leads to oxidative cellular damage that primarily results in reversible organ dysfunction as opposed to frank cellular necrosis. In these situations, the clinician routinely utilizes means of limiting cellular damage, such as the use of iced cardioplegia solution and limitations on the duration of ischemia during, for example, open heart surgery to prevent substantial cell death. In these clinical situations, reperfusion injury manifests itself as reversible organ dysfunction, including suboptimal renal function or myocardial stunning with reduced cardiac output. Substantial morbidity in the post-operative period may be associated with this transient organ dysfunction, directly increasing health care costs and risks of serious post-surgical complications.

Other clinical situations can lead to frank cell death overlayed with reversible dysfunction. Examples of ischemia followed by reperfusion resulting in tissue necrosis include, for example, myocardial infarction, drownings, stroke, and bowel infarction. The actual amount of cell death is dependent on the duration of ischemia and basal oxygen demand of the involved tissue. Theoretically, the percentage of ischemic tissue which will eventually infarct during ischemia, upon reperfusion, and during a number of hours following reperfusion will depend on the length of ischemia if all other factors are held constant. Transient ischemia of, for example, less than 10 to 15 minutes will likely not result in significant cell death within the post-ischemic zone although reversible dysfunction, such as myocardial stunning, will likely be observed. As the ischemic period lengthens, infarct size relative to area at risk continues to increase; and at some point ischemia will be so prolonged that virtually all of the area at risk will infarct regardless of whether reperfusion is eventually achieved.

In the case of a heart attack, for example, thrombolytic therapy with such agents as t-PA or streptokinase only appear effective in limiting infarct size if reperfusion of ischemic heart tissue is accomplished within about six hours of the initiation of ischemia. If ischemia persists for more than about six hours, irreversible damage, i.e., infarction of the ischemic area, has progressed maximally, and reperfusion thereafter is a futile effort. In clinical situations where infarction is to be expected after reperfusion but where the infarct size involves substantially less than the total area at risk, one can observe reversible organ dysfunction overlaid upon infarction. Tissue peripheral to the infarct zone but still lying within the ischemic zone will in these situations usually experience stunning. In the case of a myocardial infarction, if one were to monitor cardiac function in the post-reperfusion period, it would be common to see a slow rise in function over a number of hours up to possibly two days, with function returning to less than 100 percent of pre-ischemic values. The slow improvement in function reflects reversal of myocardial stunning. Irreversible cardiac damage (infarction) accounts for the failure of function to return to the pre-ischemic baseline. Morbidity in the immediate post-infarct period therefore reflects myocardial stunning overlaid upon infarction. Efforts to reduce stunning and/or infarct size both possess clinical utility in these situations.

As clinical situations involving ischemia and reperfusion, which result primarily in reversible organ dysfunction (stunning) are generally iatrogenic and therefore predictable, such as open heart, coronary bypass or organ transplantation surgery, pretreatment with medicinal agents designed to ameliorate reperfusion injury before induction of ischemia is both possible and desirable. Pretreatment allows drug effect to fully develop whether that effect may be, for example, antioxidant enzyme induction, or neutrophil desensitization. Pretreatment also avoids the problem of getting the drug past the vascular occlusion or to globally ischemic organs. Pretreatment would, of course, require that the drug display long lasting protective ability, ideally of at least 24 hours in duration.

Ischemia-reperfusion situations where significant infarction can be expected, including, for example, a heart attack, stroke, bowel infarction, and some traumatic amputations are, of course, not predictable events. As such, these clinical situations preclude pretreatment with reperfusion injury protective agents. Agents used in such situations would require that protection be achieved with drug administration immediately prior to, at the time of, or soon after reperfusion. The use of reperfusion injury protective agents in these stat clinical situations would be further restricted by the duration of the ischemic event. Ischemic events of much longer than six hours likely preclude salvaging of post-ischemic tissue as infarct size has already maximally progressed during the ischemic period.

The method of the present invention provides for the administration of a composition disclosed herein at a time interval prior to the initiation of reperfusion sufficient to permit said composition to be diffused throughout the patient's body and particularly the affected organ(s). This permits the complex, and not fully understood, cascade of events to occur which are responsible for the prophylactic and therapeutic effects observed. Administration ideally should be a period of from about 72 hours prior to an ischemic event up to about six hours after the ischemic event. If a composition of the present invention is to be administered prior to the ischemic event, it is preferred that administration be completed at least 24 hours before the ischemic event. However, in cases of an unplanned ischemic event such as heart attack, etc., it has been found that in order to achieve the advantages of use of the compositions of the present invention, they must be administered as soon as possible after an unplanned ischemic event. Preferably, administration should take place as soon as possible after the event and prior to reperfusion.

While the degree of protection is likely to be somewhat diminished, the shorter the period of time between administration of the compositions in accordance with the present invention and the onset of reperfusion, a degree of protection may be achieved by administration of the compositions in accordance with the present invention coincident with the administration of a clot dissolving medication due to the neutrophil deactivating effects of MLA and 3DMLA which appear to be quite rapid in development (Monophosphoryl Lipid A Inhibits Neutrophil Priming by Lipopolysaccharide. *J. Clin. Lab. Med.* 116:237, 1990).

The following examples are offered to further illustrate but not limit both the compositions and the method of the present invention. It is to be understood that the rat, dog, pig and rabbit models presented herein are representative of warm blooded mammals and correlate reasonably with events for other warm blooded animals, including humans.

EXAMPLE I

This example demonstrates the protective ability of 3DMLA from global ischemia induced reperfusion injury, including infarction and stunning, utilizing an isolated rat heart model.

Animals were pretreated with 3DMLA (5.0 mg/kg intraperitoneally) 24 hours before heart isolation. Hearts were surgically removed, placed in buffer solution at 37° C., and perfused with an oxygenated cardioplegic solution (Krebs-Henseleit solution). Catheters were placed in the left ventricle to measure ventricular developed pressure (dp/dt) and heart rate and the beating hearts allowed to equilibrate. Upon cardiac contractility stabilization, global ischemia was induced in the heart and allowed to persist for 35 minutes, which was followed by one hour of reperfusion.

Hearts removed from rats pretreated with 3DMLA 24 hours before surgery returned to approximately 80 percent of pre-ischemic control baseline and 60 percent of 3DMLA pre-ischemic baseline ventricular developed pressure in comparison with vehicle treated control hearts, which recovered to 26 percent of pre-ischemic control baseline function (FIG. 1). Interestingly, it was also noted that baseline cardiac contractile force, dp/dt, and heart rate were consistently higher in MLA pretreated animals when compared with controls. This positive inotropic and chronotropic effect of 3DMLA on isolated rat heart preparations suggests a direct effect on myocardial tissue of a prolonged nature.

Interestingly, in studies conducted by other investigators, lipopolysaccharide at cardioprotective doses administered 24 or 72 hours prior to heart isolation did not cause a positive inotropic and chronotropic activity in the isolated rat heart. In fact, the investigators found that optimally protective doses of lipopolysaccharide in the isolated, perfused rat heart were those dose levels which directly depress cardiac function in the pretreatment period.

The dose of 3DMLA which produced protection in this model is, on a per kilogram of body weight basis, quite high, and one should not extrapolate these results to define a protective human dose.

EXAMPLE II

This experiment was conducted to demonstrate the protective effects of the compositions of the present invention against infarct after ischemia followed by reperfusion in an intact pig model.

Experiment Protocol

Male Yorkshire pigs weighing 25-35 kg were acclimated to a 12 hour light-dark cycle for at least one week before evaluation. The light cycle began at roughly 0600 hours. The animals were maintained on standard laboratory chow and water ad lib. Twenty-four hours prior to surgery, vehicle (0.5% triethylamine in normal saline) or drug (MLA or 3DMLA) was infused over fifteen minutes into conscious, sling-restrained pigs via an ear vein. Vehicle and drugs were warmed to approximately 50° C., shaken vigorously, and diluted to roughly 50 ml in 5% dextrose/95% sterile water prior to administration. The dose for the test drugs was 0.3 mg/kg of body weight.

Following an overnight fast, the animals were lightly sedated with ketamine (22 mg/kg), acepromazine (1.1 mg/kg), and serotol (minimum effective dose). The animals were then intubated, connected to a respirator, and ventilated with 1.5% ethrane and pure oxygen. After deep anesthesia was established, a catheter was placed in the right femoral artery for measuring blood pressure. Blood pressure was monitored using a Statham pressure transducer. Sterile saline containing 2 USP units heparin/ml were also infused at a slow rate (roughly 10 ml/hr) via the arterial catheter to maintain the patency of the catheter. A catheter was also placed in the right femoral vein.

After placement of the arterial and venous catheters, surface electrodes were attached for Lead II electrocardiographic measurements. The pericardial cavity was then exposed via a left thoracotomy. (2 mg succinyl choline was administered immediately prior to performing the thoracotomy.) After exposing the heart, a Millar pressure transducer was introduced into the lumen of the left ventricle via the left atrium. The transducer was used to measure left ventricular systolic, end-diastolic and developed pressure, and the rate of pressure development ($+dp/dt_{max}$).

The first branch of the left circumflex coronary artery was then isolated immediately distal to its origin. Lidocaine (60 mg) was administered intravenously one minute prior to occluding the artery. The artery was transiently occluded using a snare occluder. Hemodynamic and electrocardiographic measurements were made prior to induction of ischemia and at fifteen minute intervals during the ischemic phase of the experimental protocol.

After 60 minutes of regional ischemia, the occlusion was removed and the artery reperfused for an additional 300 minutes (60 mg of lidocaine was administered one minute prior to reperfusion). Hemodynamic and electrocardiographic measurements were made at thirty minute intervals during the period of reperfusion.

At the conclusion of the reperfusion phase the heart was fibrillated electrically, excised and placed in ice cold saline. The size of the myocardial infarct was determined using the in vitro dual staining procedure described by Romson, et al., *J. Cardiovasc. Pharmacol.* 4:187, 1982. A 19 ga catheter was inserted into the first branch of the left circumflex coronary artery immediately distal to the site of occlusion. (The artery immediately proximal to the catheter was occluded with silk suture). A 0.5 cm cannula was placed into the aorta above the coronary ostia. The left circumflex coronary artery bed was perfused with 1.5% triphenyltetrazolium (TPT) in 20 mM potassium phosphate buffer (pH 7.4). The aorta was perfused in a retrograde manner with 0.25% Evans blue. Both solutions were perfused simultaneously at a constant pressure of 100 mmHg for 5 minutes.

After perfusion staining, the heart was sliced into 1.0 cm sections perpendicular to the apex-base axis. The area of left ventricle at risk of infarction was identified by the presence of TPT stain (except for the infarcted tissue, which was not stained). Non-ischemic myocardial tissue was stained with Evans blue. For each slice the non-ischemic area, area at risk, and infarcted areas were carefully traced onto clear acetate sheets. Both sheets were then photocopied and the different areas cut out and weighed. For individual slices, the areas obtained from tracing the top and bottom faces were averaged. Romson, et al., *J. Cardiovasc. Pharmacol.* 4:187, 1982, have previously reported that comparison of results obtained quantitating infarct size using a similar procedure (planimetry), and using gravimetric analysis indicates a significant correlation between the two methods.

Statistical Analysis

Changes in cardiovascular hemodynamic performance were evaluated in two ways. For each of the four treatment groups indices of hemodynamic performance obtained during the ischemic and reperfusion phases were compared to values obtained during the pre-ischemic phase of the protocol (within group analysis). In addition, for each time interval studied, indices of hemodynamic performance obtained for each of the drug pretreated groups were compared with the values obtained in animals pretreated with vehicle (between group analysis). Statistical significance was calculated using the Student's t-test, as described by Tallarida and Murray, *Manual of Pharmacologic Calculations with Computer Programs*, Second Edition, Springer-Verlag, New York, 1987. Differences that reached a level of $p < 0.05$ were deemed statistically significant.

Figure 2:
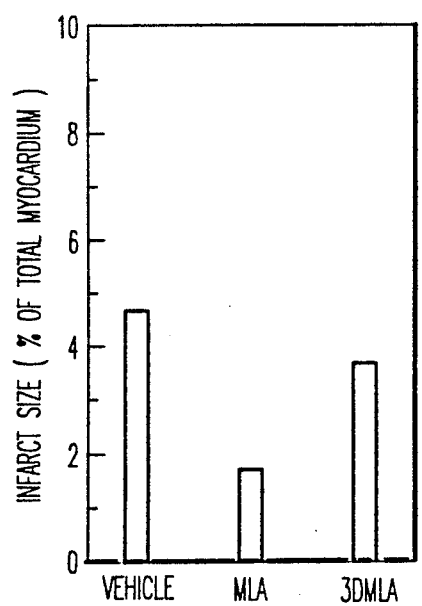
FIGS. 2 and 3 shows bar graphs demonstrating area at risk and infarct area data for MLA and 3-deacylated MLA (3DMLA) versus untreated test subjects.
Figure 3:
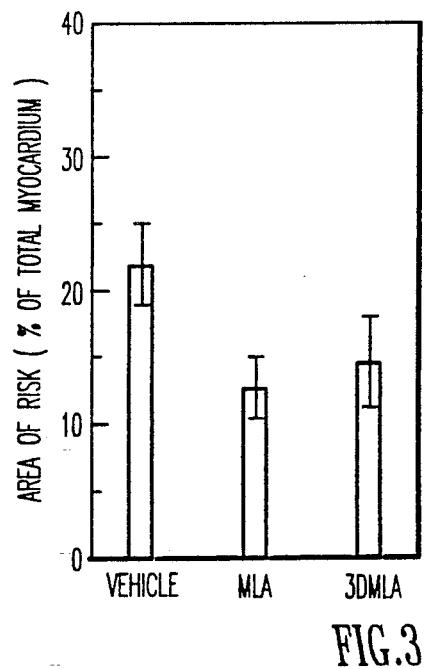

As can be seen by reference to FIG. 2, animals pretreated with MLA displayed a reduction in infarct size as a percentage of total myocardium of 63% when compared to control animals. Animals pretreated with 3DMLA showed an 18% reduction. It was also unexpectantly observed that the area at risk (ischemic zone) was significantly smaller in pigs treated with MLA or 3MLD when compared with vehicle control pigs (FIG. 3). These data indicate the test materials when administered in accordance with the present invention reduce the degree of tissue necrosis associated with normothermic ischemia followed by reperfusion. The reduction in area at risk suggests that various forms of the composition of the present invention may be improving collateral blood flow to "ischemic" or "post-ischemic" areas of the heart.

EXAMPLE III

This experiment demonstrates the effectiveness of the compositions of the present invention to prevent reversible organ dysfunction (stunning) in instances were the ischemic period is such as to preclude infarction.

Mongrel dogs were pretreated intravenously with 35 ug/kg of 3DMLA 24 hours before initiation of the surgical procedure. The left anterior descending coronary artery was ligated in this open chest anesthetized animal model for a period of 15 minutes. Animals were subsequently reperfused for three hours. Hemodynamic measurements were evaluated throughout the experiment. Two sets of sonomicrometers were inserted into the cardiac wall, one set located within the ischemic zone and one set in normally perfused tissue. Contractility was measured at baseline during ischemia and throughout the three hours of reperfusion. Endocardial and epicardial blood flow were evaluated using radiolabeled microspheres before and during ischemia and after reperfusion. In situ, pre-ischemic cardiac function of animals pretreated with 3DMLA was considerably greater than that of control animals as had been previously observed in the isolated rat heart model. Heart rate, mean arterial pressure, dp/pt, and systolic shortening in the normal zone were all increased in animals pretreated with 3DMLA. After ischemia, myocardial stunning was less severe in animals pretreated with 3DMLA with less dyskinesis during the ischemic period and an accelerated return to baseline function.

Referring to Table 1, dogs pretreated with 3DMLA returned to approximately 90 percent of baseline contractility within 180 minutes, while controls recovered to only 50 percent of function in the same period of time. Control dogs, in the inventor's experience, require approximately 24 hours to consistently recover to the same degree of contractility as achieved within three hours of reperfusion in animals pretreated with 3DMLA.

before the start of the experiment with either 0.2% triethylamine in water for injection vehicle (control) or the test composition 3DMLA in the same vehicle administered by intravenous injection using the marginal ear vein. Anesthesia was induced with ketamine hydrochloride (30 mg/kg) and xylazine hydrochloride (3 mg/kg) administered by intramuscular injection. Additional injections of the anesthetic agents were given as necessary to maintain anesthesia throughout the experimental protocol, as evaluated by frequent toe-pinch method and the presence of a medial palpebral reflex. Following induction of anesthesia, catheters were placed in the common carotid arteries, and a tracheostomy was performed. Rabbits were ventilated within their normal respiratory values (tidal volume=5 ml/kg; rate=50/minute). The heart was exposed by a left lateral thoracotomy. The left anterior descending (LAD) coronary artery, at a location just distal to the left auricular appendage, was ensnared by an encircling silk suture. The suture was then threaded through a small button and then through a length of small plastic tubing (5 cm long, 1 mm inside diameter, 2 mm outside diameter). Myocardial ischemia was induced by clamping the suture under tension at a position directly adjacent to the end of the plastic tubing with a hemostatic forceps. Following baseline measurements a 90 minute period of myocardial ischemia was maintained. At the end of the ischemic period the hemostatic forceps were released, and the plastic tubing and button were removed from the suture. The heart was then reperfused for a period of 3 hours. The rabbit was euthanized in a humane manner using an overdose of the anesthetic delivered by the intracardiac catheter, following the three hour reperfusion period.

Parameters measured at specific times during the experimental protocol were heart rate, arterial blood pressure, left ventricular pressure, (dp/dt), lead II electrocardiogram (EKG), and enzyme levels of creatinine phosphokinase (CPK). Following completion of the experimental protocol and euthanasia of the rabbit, the heart was excised. Determination of the myocardial

TABLE 1

Canine Myocardial Stunning After Transient Regional Ischemia Followed by Reperfusion Rates of Recovery from Reversible Myocardial Stunning

| | Percent Myocardial Segment Shortening $\left(\frac{ED-ES}{ED}\right) \times 100^{1,2}$ | | Percent Recovery Myocardial Contractility$^2$ | |
|---|---|---|---|---|
| | Treatment | | Treatment | |
| Time During Study | Controls | 3DMLA 35/ug/kg | Controls | 27 3DMLA 35 ug/kg |
| Baseline (preischemia) | 29% | 28% | N/A | N/A |
| 12 minutes ischemia | −6% | −1% | −20.7% | −3.6% |
| Post ischemia | | | | |
| 50 minutes | 7% | 11% | 24.1% | 39.3% |
| 100 minutes | 17% | 23% | 58.6% | 82.1% |
| 180 minutes | 15% | 25% | 51.7% | 89.3% |

$^1$ED - end diastolic length,
ES - end systolic length
$^2$Values reported for ischemic zone myocardial tissue - no significant changes observed in non-ischemic zone tissues during study period.

This experiment was conducted to further demonstrate the protective effects of the compositions of the present invention in another in vivo model.

Methods

New Zealand White rabbits of either sex were utilized in this study. The rabbits were pretreated 24 hours area of ischemia and the size of the myocardial infarct was performed by an in vitro dual perfusion technique. Cannulae were placed into the LAD coronary artery immediately distal to the site of the LAD occlusion and into the aorta just above the coronary sinus. The LAD coronary vascular bed was perfused with 1.5% triphenyltetrazolium (TPT) in 20 mM potassium phosphate buffer (Ph 7.4, 37° C.). The aorta was perfused in a retrograde manner with 0.9% saline. Both solutions were perfused simultaneously through their respective cannulae at a constant pressure of 100 mm Hg for 5 minutes. The heart was then frozen and sliced into transverse sections for photographic evaluation.

Results

Serum CPK levels were evaluated at baseline, 90 minutes ischemia, 60 minutes reperfusion, and at 180 minutes reperfusion for control, 35 ug/kg 3DMLA, 60 ug/kg 3DMLA and 100 ug/kg 3DMLA pretreatment groups. The baseline values of 225±66, 250±79, 200±54, and 221±67 units/ml, respectively, for control, 35 ug/kg, 60 ug/kg and 100 ug/kg 3DMLA pretreatments were equal showing no significant difference between groups.

As can be seen by reference to Table 2, serum CPK levels in animals pretreated with 3DMLA at doses of 35, 60 or 100 ug/kg showed a consistent trend of decreased serum CPK following ischemia and reperfusion indicating protective activity against irreversible cardiac damage (infarction) attributable to ischemia and reperfusion.

TABLE 2

Effect of Pretreatment with 3DMLA on CPK Serum Levels
CPK serum levels (units/ml)

|  | Controls | 3DMLA (35 ug/kg) | 3DMLA (60 ug/kg) | 3DMLA (100 ug/kg) |
|---|---|---|---|---|
| Baseline | 225 ± 66 | 250 ± 79 | 200 ± 54 | 221 ± 67 |
| 90 min. Ischemia | 342 ± 89 | 302 ± 71 | 270 ± 84 | 277 ± 60 |
| 60 min. Reperfusion | 420 ± 83 | 347 ± 85 | 313 ± 78 | 337 ± 108 |
| 180 min. Reperfusion | 572 ± 137 | 405 ± 130 | 422 ± 176 | 385 ± 102 |
|  | N = 12 | N = 11 | N = 14 | N = 7 |

Table 3, which measures double product hemodynamic values (left ventricular developed pressure [LVDP] times heart rate÷1000), shows that control group animals experienced a steady continual decline in double product values throughout the period of reperfusion, indicating substantially reduced cardiac function, whereas animals treated with 3DMLA at a dosage of 35 or 60 ug/kg had higher and stabilized double product values, indicating a reduced degree of cardiac dysfunction at all times of reperfusion in comparison with control animals. Another remarkable finding was that unlike control hearts, 3DMLA treated hearts did not show continuing deterioration of function between 90 and 180 minutes of reperfusion.

TABLE 3

Effect of Pretreatment with 3DMLA on Haemodynamics
Double Product Haemodynamics (LVDP × HR/1000)

|  | Controls | 3DMLA (35 ug/kg) | 3DMLA (60 ug/kg) |
|---|---|---|---|
| Baseline | 15.43 ± 2.59 | 14.21 ± 4.05 | 14.06 ± 1.91 |
| 15 min. Reperfusion | 8.94 ± 2.44 | 13.00 ± 3.47 | 11.19 ± 1.80 |
| 90 min. Reperfusion | 7.14 ± 1.49 | 11.99 ± 3.01 | 9.72 ± 3.60 |
| 120 min. Reperfusion | 7.15 ± 1.40 | 10.69 ± 3.42 | 9.91 ± 2.82 |
| 150 min. Reperfusion | 6.94 ± 1.11 | 10.94 ± 2.82 | 10.50 ± 2.60 |
| 180 min. Reperfusion | 6.49 ± 1.83 | 11.70 ± 2.81 | 10.20 ± 2.20 |

TABLE 3-continued

Effect of Pretreatment with 3DMLA on Haemodynamics
Double Product Haemodynamics (LVDP × HR/1000)

|  | Controls | 3DMLA (35 ug/kg) | 3DMLA (60 ug/kg) |
|---|---|---|---|
|  | N = 14 ($t_o$) | N = 6 ($t_o$) | N = 6 ($t_o$) |

In addition to the foregoing, the mean area at risk and mean infarct area of control group animals and animals pretreated with 3DMLA at a dosage of 60 ug/kg were measured. Hearts from control animals showed a mean risk area of 39.2% of total myocardium and a mean infarct area of 5.2% of total myocardium. Hearts from animals pretreated with 3DMLA showed a mean risk area of 30.9% and a mean infarct area of 1.6% (70% decrease in infarct size), which is consistent with the CPK and double product values discussed above and which further validate the significant protective ability of the compositions of the present invention.

From the foregoing examples, it can be seen that compositions and method embodied by the present invention are effective to prevent or ameliorate the harmful effects associated with ischemia followed by reperfusion of blood flow, thereby accomplishing the objectives stated herein. It is to be understood that the foregoing examples are illustrative of the present invention and are not intended to include all possible variations thereof. Certain modifications of the compositions and/or methods employed may be made and still achieve the objectives of the invention. Such modifications are contemplated as within the scope of the claimed invention.

What is claimed is:

1. A method for the amelioration of organ tissue injury in warm blooded animals caused by reperfusion of blood flow to the organ following a period of ischemia, which method comprises administering to a warm blooded animal prior to a medical procedure normally causing ischemia followed by reperfusion an effective amount of a pharmaceutical composition comprising a refined detoxified endotoxin selected form the group consisting essentially of monophosphoryl lipid A and 3-deacylated monophosphoryl lipid A and a pharmaceutically acceptable carrier.

2. The method of claim 1 wherein the pharmaceutical composition is administered to the warm blooded animal form about 72 hours prior to the onset of ischemia to about 6 hours after the onset of ischemia.

3. The method of claim 2 wherein the amount of pharmaceutical composition administered to the warm blooded animal is such that the amount of refined detoxified endotoxin administered is from about 1.0 micrograms to about 100 micrograms per kilogram of body weight.

4. The method of claim 2 wherein the amount of pharmaceutical composition administered to the warm blooded animal is such that the amount of refined detoxified endotoxin administered is from about 1.0 micrograms to about 35 micrograms per kilogram of body weight.

5. The method of claim 2 wherein the amount of pharmaceutical composition administered to the warm blooded animal is such that the amount of refined detoxified endotoxin administered is under 20 micrograms per kilogram of body weight.

6. The method of claim 2 wherein the refined detoxified endotoxin is monophosphoryl lipid A.

7. The method of claim 2 wherein the refined detoxified endotoxin is 3-monophosphoryl lipid A.

8. The method of claim 2 wherein the pharmaceutical composition is administered intravenously.

9. The method of claim 2 wherein the pharmaceutical composition is administered intramuscularly.

10. The method of claim 9 wherein the pharmaceutical composition is administered tot he warm blooded animal from about 24 hours prior to the onset of ischemia up to the onset of ischemia.

11. The method of claim 9 wherein the medical procedure is a surgical event and is selected form the group consisting of cardiac surgical procedures, organ transplants, traumatic limb amputation and reattachment.

12. The method of claim 9 wherein the medical procedure involves an ischemic reperfusion event said event being selected from the group consisting of gut infarct and myocardial infarct.

* * * * *